United States Patent [19]

Shelton et al.

[11] 4,160,114

[45] Jul. 3, 1979

[54] CO-CATALYTIC METHOD FOR OBTAINING IMPROVED CHLORINATION OF PHENOLS

[75] Inventors: Frederic J. Shelton, Tacoma; William H. Wetzel, Federal Way; John E. Wilkinson, Gig Harbor; Robert J. Goodwin, Puyallup, all of Wash.

[73] Assignee: Reichhold Chemicals, Inc., White Plains, N.Y.

[21] Appl. No.: 817,439

[22] Filed: Jul. 20, 1977

[51] Int. Cl.$^2$ .................. C07C 39/36; C07C 37/00
[52] U.S. Cl. ................................. 568/776; 568/779
[58] Field of Search ............ 260/623 H, 625, 648 H; 568/779, 776

[56] References Cited

U.S. PATENT DOCUMENTS

| | | | |
|---|---|---|---|
| 2,131,259 | 9/1938 | Stoesser | 260/623 H |
| 3,426,035 | 2/1969 | Bremmer | 260/62 EH |
| 3,920,757 | 11/1975 | Watson | 260/623 H |

FOREIGN PATENT DOCUMENTS

| | | | |
|---|---|---|---|
| 230337 | 9/1968 | Australia | 260/649 |
| 948601 | 2/1964 | United Kingdom | 260/623 H |

*Primary Examiner*—Werren B. Lone

[57] ABSTRACT

In a process for producing relatively pure commercially acceptable pentachlorophenol, comprising reacting, at a temperature ranging from about 10° to about 190° C., (A) a phenol consisting essentially of raw or commercial phenol which may contain, as impurities from other processes, some lower chlorophenols such as mono and dichlorophenols and mixtures thereof, and (B) chlorine, in the presence of (C) an acid catalyst from about 0.005 moles to about 0.016 moles per mole of (A) used, consisting essentially of aluminum chloride, ferric chloride, metal iron, aluminum tributoxide, antimony chloride, metallic antimony, stannous chloride, metallic tin, cuprous chloride and metallic copper; the improvement consisting of using (D) a sulfur containing co-catalyst selected from the group consisting of sulfur, thiophenol, para-chlorothiophenol, para, para'-dichlorophenyl sulfide, sodium hydrosulfide, 2,2'-thiobis (4,6-dichlorophenol) benzyl disulfide, dibenzothiophenol, benzyldisulfide, diphenyl sulfide, diphenyl disulfide, di-isopentyl sulfide, naphthalene thiol, heptyl sulfide, hexochlorophenyl sulfide, dicresyl disulfide, dihexadecyl sulfide and dibenzothiophenol thiophenol, wherein components (A) and (B) constitute the sole reacting ingredients and components (C) and (D) constitute the catalytic system for promoting the reaction of components (A) and (B).

7 Claims, No Drawings

CO-CATALYTIC METHOD FOR OBTAINING IMPROVED CHLORINATION OF PHENOLS

This invention relates to the use of a novel co-catalyst in conjunction with acid catalysts generally used in producing chlorinated phenols. These novel co-catalysts consist of one or more sulfur containing compounds such as thiophenol and diphenyl sulfide used generally in extremely small amounts.

Some of the advantages gained include reduced chlorination times, increased manufacturing safety by reducing the risk of unexpected and violent evolution of hydrochloric acid and increased yields of the desired chlorinated product. Furthermore, starting materials may include phenols which are otherwise difficult or impossible to chlorinate using standard catalysts and conditions.

This invention relates to an improved method of preparing relatively pure higher chlorinated phenols and especially pentachlorophenol by catalytic means. Among the benefits realized are a reduction of impurities such as chlorinated dibenzo-p-dioxins and chlorinated dibenzofurans. In the previously described processes for chlorination of phenols or partially chlorinated phenols to form higher chlorinated phenols such as pentachlorophenol, the customary practice is to employ such catalysts as metal aluminum chloride, aluminum, antimony pentachloride, ferric chloride and iodine. Following chlorination, the molten chlorophenols are pumped to heated storage pending flaking, prilling, or molding operations necessary to change the product to a form acceptable for end use. Some of the specifications for industrial chlorinated phenols valuable for fungicidal activity are low alkali insoluble content, low insolubles in alkane solvents as well as, in the case of pentachlorophenol, a minimum of 86% pentachlorophenol content.

The use of aluminum chloride alone works adequately in most instances, however, there is encountered from time to time in manufacture of particular batches, depending on the source or quality of the raw materials, a problem of unreactivity leading to prolonged chlorination time and the usual consequences of lowered quality of the final product and the danger of a sudden explosive release of hydrochloric acid gas during chlorination.

It has been found that re-distilled lower chlorinated phenols in particular give chlorination problems in their employment as raw material for manufacture of pentachlorophenol and frequently different supplies of phenol vary in time required to chlorinate them to higher chlorinated phenols. In some instances, it is impossible to successfully chlorinate phenol into acceptable pentachlorophenol without the use of our invention.

It is among the objects of this invention to provide a process whereby relatively pure commercially acceptable higher chlorinated phenols such as pentachlorophenol are produced under safe operating conditions at all times by use of a powerful catalyst system and wherein the desired product specifications can be met. It is also an object of this invention to reduce the polymeric by-products normally present in higher chlorinated phenols such as pentachlorophenol. A number of co-catalysts were used in conjunction with aluminum chloride and were evaluated to discover more effective catalyst systems. Initially, combinations of aluminum chloride and other metallics were tried as co-catalysts. Experiments were conducted by adding nickel chloride along with the usual aluminum chloride to a nonreactive batch of phenol and chlorinating to obtain pentachlorophenol. No beneficent effect could be noted by adding the nickel compound and, in fact, the reaction would not be completed. In another experiment, ferric chloride was added along with the aluminum chloride. It was observed that the ferric chloride addition did help in the reaction since less chlorine was by-passed in the off-gas vent. The reaction time was still 9.5 hours as compared to the control of 9.5 to 10.5 hours; a small gain in the reaction time. It was also observed that ferric chloride gave rise to more alkali insolubles in the final product. When ferric chloride was tried in the plant, the advantage gained was insufficient to relieve the problem of unreactive phenol or partially chlorinated phenols in batches used as the starting material for the manufacture of pentachlorophenol. In other experiments, copper and zinc salts were tried without significant success.

Because of this limited success in finding a successful metallic co-catalyst, we were surprised to find that thiophenol, when added with anhydrous aluminum chloride, significantly reduced the reaction time. In addition, it was discovered that dangerous dips were avoided in the plant process. Further investigation of this phenomenon revealed that thiophenol alone will not catalyze chlorination of phenols to higher chlorinated phenols. It is theorized, after this discovery, that the thiophenol in some way formed a complex with aluminum chloride; this complex being a powerful chlorinating catalyst. Other explanations could be possible. Investigation of the literature revealed that thiophenol in the presence of aluminum chloride forms diphenyl sulfide and thus it was probably this particular sulfur compound that we were mainly concerned with when attempting to elucidate reasonable mechanisms that can explain its role in the chlorinating reaction. We further realized that during chlorination, diphenyl sulfide would, itself, be chlorinated on the ring structure; for instance, to tetrachlorodiphenyl sulfide.

It would appear from the above considerations and background that when diphenyl sulfide is added along with aluminum chloride in the reaction mixture at some time during the reaction, the chlorinated diphenyl sulfide-aluminum chloride molecular addition compound is formed. This can be regarded as a metal ligand bond, as for example, shown below:

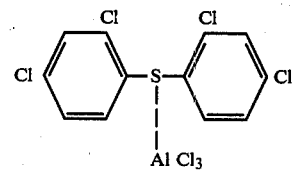

The commonly accepted mechanism for aromatic halogenation in the presence of aluminum or iron chloride implies the chlorinating agent is the chlorinium ion (Cl+); this particular species being necessary for the reaction to proceed.

It is possible that the high chlorinating activity demonstrated in our invention may be due to the formation of relatively high concentrations of the chlorinium ion from the interaction of a sulfide-aluminum chloride complex with chlorine as in the example on the following page.

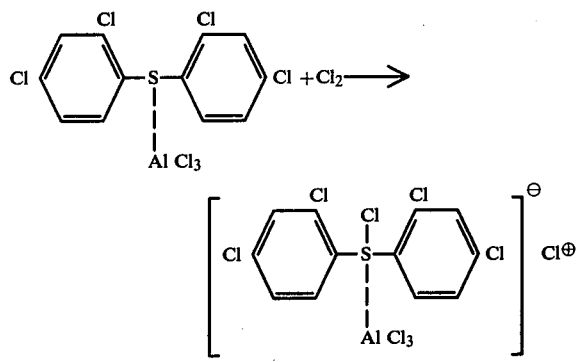

Other explanations for the powerful and unique chlorinating activity of the catalyst systems of our invention may also be devised, but these considerations which were not obvious prior to our catalyst discovery do not detract from the scope and utility of this discovery.

Through use of our invention, it is now possible to manufacture highly chlorinated phenols such as pentachlorophenol in shorter reaction times with improved quality of the product. Still another important benefit is avoidance of "dips" when the chlorination reaction virtually ceases followed by violent evolution of hydrochloric acids. In plant process, danger to life of the workers arises when a batch erupts during a bad "dip".

Normally, chlorine time reactions may be carried out with or without a solvent at temperatures gradually increasing up to about 190° C. The preferred amount of catalyst which we employ is from about 0.0001 moles to about 0.02 moles of the sulfide, sulfur or sulfhydryl and from about 0.001 to about 0.004 moles of aluminum chloride per mole of phenol or partially chlorinated phenol starting material. However, it has been found that from between 0.000015 moles and about 0.2 moles of the sulfide, sulfur or sulfhydryl may be used and from about 0.0005 to about 0.016 moles of aluminum chloride per mole of phenol or partially chlorinated phenols may be used.

As well as aluminum chloride, other forms of aluminum can be employed in the practice of this invention such as aluminum metal itself or organic compound of aluminum. Aluminum and/or its derivatives revert to or form aluminum chloride by chemical reaction with elemental chlorine which is introduced into the reactor during the manufacturing process. In addition, the following metal catalysts may be used in place of aluminum metal or aluminum chloride in essentially the same amount: ferric chloride, metal iron, aluminum trisbutoxide, antimony chloride, metallic antimony, stannous chloride, metallic tin, cuprous chloride and metallic copper.

Typical sulfur bearing compounds that can be used as part of this invention include sulfur, diphenyl sulfide, diphenyl disulfide, dicresyl disulfide, dihexadecyl sulfide and dibenzothiophenol thiophenol, parachlorothiophenol, para, paradichlorophenyl sulfide, sodium hydrosulfide, 2,2'-thiobis (4,6-dichlorophenol) benzyl disulfide, diisopentyl sulfide, naphthalene thiol, heptyl sulfide and hexachlorophenyl sulfide.

As previously stated, another object of this invention is to provide a process for producing pentachlorophenol containing considerably reduced amounts of undesirable polymeric impurities. Among these are certain chlorinated dibenzodioxins and chlorinated dibenzofurans that normally occur in the regular manufacturing processes. These chlorinated dibenzodioxins have been considerably studied and occur in the range of 100 to 5000 parts per million total in commercial technical grade pentachlorophenol. This mixture of chlorinated dibenzo-p-dioxins has been analyzed and found to consist of hexachlorodibenzo-p-dioxins (2 isomers, the 1,2,3,7,8,9 and 1,2,4,6,7,9-hexachlorodibenzo-p-dioxins), heptachlorodibenzo-p-dioxin (2 isomers, the 1,2,3,4,6,7,8 and 1,2,3,4,6,7,9-heptachlorodibenzo-p-dioxins), and 1,2,3,4,6,7,8,9-octachlorodibenzo-p-dioxins. The most toxic chlorinated dibenzo-p-dioxin, the 2,3,7,8-tetrachlorodibenzo-p-dioxin was not found to be present in any instance. Following the practice of our invention, the total amounts of all chlorinated dibenzo-p-dioxins are reduced on the average to about 40% of the control, the hexachlorodibenzo-p-dioxins were reduced on the average to 24% of the control, the heptachlorodibenzo-p-dioxins were reduced on the average to 41% of the control, and the octachlorodibenzo-p-dioxin was reduced on the average to 55% of the control. The control is commercial technical grade pentachlorophenol.

Also, the chlorinated dibenzofuran concentrations in pentachlorophenol are reduced by practice of our invention. In this instance, the heptachlorodibenzofurans (isomers not elucidated) were reduced 20–40% compared to the control and 1,2,3,4,5,6,7,8-octachlorodibenzofuran was reduced about 70–94% as compared to the control.

Typically, chlorinations are carried out in a glass vessel equipped with a stirrer, heating mantle, cooling system, a thermometer, a chlorine feed line with a sintered glass diffuser and an exit line for hydrochloric acid vapor. Chlorine is fed from a chlorine cylinder to which a reducing valve was attached. A manometer containing carbon tetrachloride is connected across an orifice as a flow meter.

One kilogram samples of low reactive phenol or partially chlorinated low reactive phenol plus about 2.8 grams of anhydrous aluminum chloride or its mole equivalent of aluminum metal and 0.0001 to 0.2 moles of the sulfur or sulfur containing co-catalyst were heated to 120° C. and chlorinated to pentachlorophenol with stirring. The chlorine feed was regulated so that bypassing was minimized. The temperature was increased slowly to keep the batch molten until the freezing point reached about 178°–183° C. The batch was then poured out and quenched by solidification. The total time of chlorination and other characteristics of the batch were noted and placed in Table I. Variations of this procedure may be carried out, within keeping of the state of the art, but we found this procedure sufficiently useful for obtaining the necessary data. In other experiments, plant size batches were run in about the same manner as in the laboratory. The partially chlorinated phenols used for the experiments had been previously distilled and were found to be unreactive for the normal process of making pentachlorophenol with use of aluminum chloride catalyst alone.

The following examples illustrate the advantages and unexpected results which are achieved by use of the catalytic agents of this invention, but it is not intended that this invention be limited by or to the examples.

Examples I, II, III and IV were designed to give a comparison of the time taken to successfully complete chlorination of phenols to produce pentachlorophenol.

EXAMPLE I

In the 2000 ml vessel with other equipment as described 1000 grams of feedstock (particularly unreactive and partially chlorinated phenol), 2.8 grams of anhydrous aluminum chloride and 3.9 grams of diphenyl sulfide were heated to 120° C. and the chlorine was sparged in at a rate so that the by-passing of unreacted chlorine was minimized. The batch was heated slowly so that the temperature was 5 to 10° C. above the freezing point of the batch at any time. Samples of the batch were withdrawn from time to time and the freezing points taken and recorded. When the freezing point reached about 181° C., chlorination was stopped and the product poured out. No difficulty was encountered in completing this reaction which took 6 hours. In this example, the 6 hour recorded chlorination time is low compared to other experiments where sulfides were not used in conjunction with aluminum chloride. The low chlorination time indicates that the catalyst system is very effective and powerful whereas longer reaction time would indicate less effectiveness.

EXAMPLE II

In the same equipment as described in Example I, a mixture of 1000 grams of the same feedstock as in Example I, 2.8 grams of anhydrous aluminum chloride and no diphenyl sulfide was chlorinated as before. Unlike Example I, the chlorine feed rate had to be kept lower throughout the reaction because of extensive chlorine by-passing due to phenol unreactivity. Thus, the time for the reaction to come to completion (freezing point 179.5° C.) was 10½ hours.

EXAMPLE III

In the same equipment as described in Example I, a mixture of 1000 grams of the same feedback, 2.8 grams of anhydrous aluminum chloride, a 0.150 grams of ferric chloride was chlorinated in a manner similar to Example I to obtain a pentachlorophenol product with a freezing point of 178.6° C. The reaction time was 9¾ hours.

EXAMPLE IV

This was a series of experiments primarily testing the effects of sulfur based co-catalysts. They were run under similar conditions (as in Example I) except that the co-catalysts are varied. The effect of these co-catalysts are readily seen in Table I, the column "Total Chlorination Time" where shorter reaction time indicates a more powerful catalyst system. The amount of phenolic starting material and aluminum chloride is the same as in Example I, 1000 grams and 2.8 grams respectively. A variety of sulfur compounds as well as sulfur itself and a number of metallic salts are included in these summarized experiments. The amount of sulfide type co-catalysts are listed in Table I. The results shown in Table I demonstrate that a combination complex catalyst consisting of sulfur or sulfur bearing compounds with metallic catalysts such as aluminum chloride is a highly effective co-catalyst system for chlorination of phenols.

TABLE I

LABORATORY RATE STUDY OF PREPARATION OF PENTACHLOROPHENOL USING VARIOUS TEST CO-CATALYSTS WITH ALUMINUM CHLORIDE

| | CO-CATALYST NAME | GRAMS | FREEZING POINT FINAL OF PENTA-CHLOROPHENOL °C. | TOTAL CHLORINATION TIME, HOURS |
|---|---|---|---|---|
| 1 | (Control) none | — | 179.5 | 10½ |
| 2 | thiophenol | 4.68 | 179.0 | 6¾ |
| 3 | thiophenol | 2.36 | 179.0 | 6 |
| 4 | thiophenol | 1.20 | 178.0 | 7 |
| 5 | thiophenol | 1.00 | 179.0 | 5¾ |
| 6 | thiophenol | 0.50 | 178.0 | 6¾ |
| 7 | thiophenol | 0.10 | 181.0 | 6½ |
| 8 | thiophenol | 0.01 | 178.0 | 9 |
| 9 | p-chloro-thiophenol | 5.00 | 179.0 | 6 |
| 10 | p-chloro-thiophenol | 0.50 | 180.0 | 7¾ |
| 11 | p,p'-dichloro phenyl sulfide | 0.14 | 183.0 | 6 |
| 12 | sodium hydro-sulfide | 0.50 | 180.0 | 6½ |
| 13 | 2,2'-thiobis (4,6-dichloro-phenol) | 0.10 | 181.5 | 7½ |
| 14 | (Control) none | — | 181.0 | 9½ |
| 15 | Bis(dimethyl-0-thiocarbamoyl) disulfide | 0.13 | 181.0 | 7½ |
| 16 | dibenzothiophene | 0.10 | 180.5 | 7½ |
| 17 | benzyl-disulfide | 0.13 | 181.0 | 8 |
| 18 | diphenyl sulfide | 1.40 | 181.0 | 6½ |
| 19 | diphenyl sulfide | 1.10 | 181.0 | 6¼ |
| 20 | diphenyl sulfide | 3.90 | 181.0 | 6 |
| 21 | diisopentyl sulfide | 0.19 | 181.0 | 6¾ |
| 22 | naphtalene thiol | 0.17 | 181.0 | 6¾ |
| 23 | heptyl sulfide | 0.12 | 180.5 | 6¾ |
| 24 | sulfur | 0.02 | 181.0 | 6½ |
| 25 | hexachloro- | 0.22 | 181.0 | 7½ |

TABLE I-continued
LABORATORY RATE STUDY OF PREPARATION OF PENTACHLOROPHENOL USING VARIOUS TEST CO-CATALYSTS WITH ALUMINUM CHLORIDE

| | CO-CATALYST | | FREEZING POINT FINAL OF PENTA- | TOTAL CHLORINATION |
|---|---|---|---|---|
| | NAME | GRAMS | CHLOROPHENOL °C. | TIME, HOURS |
| | phenyl sulfide | | | |
| 26 | ferric chloride | 0.150 | 178.6 | 8¼ |
| 27 | ferric chloride | 0.075 | 178.6 | 8¾ |
| 28 | nickel chloride | 0.15 | — | —* |
| 29 | zinc chloride | 0.15 | 177.1 | 9¾ |

*Reaction failed to continue after 4¼ hours and therefore, discontinued.

EXAMPLE V

In this series of experiments, pentachlorophenol was prepared on a plant scale using from 7500 to 9000 pounds of phenol and/or partially chlorinated phenol as starting material. The conditions were essentially the same as those used for the laboratory batches but on a larger scale. Table II gives details of the experiments and results of the tests performed on the final pentachlorophenol product. Considerable improvement was observed in the runs where the co-catalyst of this invention, the sulfur derivatives, were used; as for example, in less chlorination time required and less insolubles being produced. In these experiments, about 20–70 pounds of aluminum chloride were used per batch. The type of phenolic starting material varied wherein only the unreactive phenol was used (A) or a combination of an unreactive and reactive phenol (B) was used, depicted as (A+B) in Table II.

EXAMPLE VI

In this set of experiments, in the plant the phenolic chlorination scale and conditions were set the same as for Example V where 7500 to 9000 pounds of phenol and/or partially chlorinated phenol was utilized as starting material. The aluminum chloride was the same as that described in Example V while the amounts of the sulfide co-catalyst were varied as described in Table III. It was observed that with the use of a sulfide or sulfur containing compound, the amounts of objectionable chlorinated dibenzo-p-dioxins were reduced by the following percentages as compared to commercial technical grade pentachlorophenol. The total kinds of chlorinated dibenzo-p-dioxins reduced 49%; the hexachlorodibenzo-p-dioxins reduced 24%; the heptachlorodibenzo-p-dioxins reduced 41%. Details of the Example VI experiments are shown in Table III.

TABLE II
STUDY OF PLANT BATCHES OF PENTACHLOROPHENOL WITH AND WITHOUT USE OF CO-CATALYST

| BATCH NO. | PHENOLIC STARTING MATERIAL TYPE | CO-CATALYST[b] TYPE | AMOUNT LBS. | FREEZING POINT OF FINAL PRODUCT | CAUSTIC INSOLUBLE %[c] | TOTAL CHLORINATED PRODUCT[d] | HEXANE TEST[e] | REACTION TIME, HOURS |
|---|---|---|---|---|---|---|---|---|
| 31-2-468 | A+B[a] | none | — | 178.9 | 0.40 | 96.9 | Heavy ppt. before 20 minutes | 19 |
| 34-2-468 | A+B | none | — | 179.9 | 0.33 | 96.7 | " | 19¼ |
| 37-2-468 | A+B | none | — | 179.0 | 0.50 | 95.92 | " | 19 |
| 29-2-568 | A+B | none | — | 179.5 | 0.46 | 96.8 | " | 19 |
| 31-2-568 | A+B | none | — | 179.5 | 0.80 | 96.24 | " | 19 |
| 34-2-668 | A+B | none | — | 178.0 | 0.60 | 96.00 | " | 19 |
| 6-2-768 | A[a] | none | — | 180.3 | 0.23 | 96.3 | " | 24 |
| 8-2-768 | A | none | — | 179.9 | 0.77 | 96.8 | " | 21¼ |
| 14-2-769 | A | diphenyl disulfide | 1 | 179.0 | 0.18 | 97.5 | OK | 16¾ |
| 16-2-769 | A | " | 1 | 179.0 | 0.18 | 97.3 | OK | 16¼ |
| 18-2-769 | A | diphenyl disulfide | 1 | 179.0 | 0.32 | 97.3 | OK | 17 |
| 27-2-269 | A | thiophenol | ¾ | 179.5 | 0.10 | 96.8 | OK | 16 |
| 44-2-269 | A | " | ¾ | 179.5 | 0.10 | 96.8 | OK | 16 |
| 49-2-269 | A+B | " | ¾ | 179.0 | 0.14 | 96.5 | OK | 16 |

TABLE II-continued
STUDY OF PLANT BATCHES OF PENTACHLOROPHENOL WITH AND WITHOUT USE OF CO-CATALYST

| BATCH NO. | PHENOLIC STARTING MATERIAL TYPE[a] | CO-CATALYST[b] TYPE | AMOUNT LBS. | FREEZING POINT OF FINAL PRODUCT | CAUSTIC INSOLUBLE %[c] | TOTAL CHLORINATED PRODUCT[d] | HEXANE TEST[e] | REACTION TIME, HOURS |
|---|---|---|---|---|---|---|---|---|
| 45-2-269 | A | " | ¾ | 179.8 | 0.14 | 96.5 | marginal | 17 |

[a] A = Penta feed stock which is obtained as products from distillation of chlorinated phenols. This material is known to be unreactive for preparing pentachlorophenol.
B = Recycle phenol is ordinary phenol directly obtained from tank cars and mono chlorinated in a side reactor just prior to chlorination to pentachlorophenol in the main reactor.
A+B = Combination of A and B.
[b] About 20–70 lbs. of aluminum chloride are used as co-catalyst in chlorination of about 8,500 lbs. of the phenol.
[c] The alkali-insoluble matter in pentachlorophenol is determined in the following way: Dissolve a 1-gram sample in 50 milliliters of N/1 NaOH and 50 milliliters of distilled water, warming to about 60° C. and crushing larger particles with flattened glass rod. Filter through a tared Gooch crucible with asbestos mat, wash free from alkali with distilled water, and dry at 100° C. to constant weight. The increase in weight represents alkali-insoluble matter.

$$\frac{\text{Grams residue} \times 100}{\text{Grams of a sample}} = \text{percent alkali insolubles}$$

[d] The total chlorinated phenols are determined in the following way: The total chlorinated phenol content is determined by titration of dry pentachlorophenol with sodium hydroxide.
Reagents -
(a) $CO_2$-free 95 percent ethyl alcohol.
Note:
Ethyl alcohol denatured according to formula 2B of the appendix to Regulations No. 3, Formulae for Completely and Specially Denatured Alcohol is suitable for this purpose. Distill the ethyl alcohol (formula 2B) over caustic pellets. Store in a stoppered bottle.
(b) Meta cresol purple indicator solution. Place 0.100 grams of meta cresol purple in a small mortar, add 2.62 milliliters of N/10 aqueous NaOH. Rub with the pestle until solution is complete. Transfer the solution to a 100-milliliter volumetric flask and make up to volume with distilled water.
Procedure
Weigh a 1.0000-gram sample and transfer to a clean 250-milliliter Erlenmeyer flask. Add 65 milliliters of ethyl alcohol and gently swirl until solution of the sample is complete. Add 35 milliliters of distilled water and subtract from above titration.
Net ml. of N/10 NaOH × 0.02663 × 100 = Total chlorinated phenols as percent pentachlorophenol.
Note:
Ethyl alcohol solutions pick up $CO_2$ from the air fairly rapidly, therefore, titrate sample immediately after dissolving in the alcohol.
[e] The hexane test consists of dissolving 2.5 grams of the pentachlorophenol in 2.5 ml of methanol (with warming) and then adding the solution with stirring to 50 mls of hexane. The solubility test passed if no precipitate forms in 20 minutes.

EXAMPLE VII

In this experiment, pentachlorophenol was prepared in the manner described in Example VI, but in this case, the presence of chlorinated dibenzofurans were checked analytically by use of mass spectrometry methods in both the test and control batches. Heptachlorodibenzofuran (isomers not identified) was reduced 20–40% and 1,2,3,4,5,6,7,8-octachlorodibenzofuran was reduced 70–94% when diphenyl sulfide was employed with aluminum chloride as the catalyst system as compared with the control tests.

TABLE III
SHOWING REDUCED CHLORINATED DIOXINS USING DIPHENYL SULFIDE AS INHIBITOR AGENT IN MANUFACTURE OF PENTACHLOROPHENOL

| BATCH NO. | FORM OF PENTACHLOROPHENOL MANUFACTURE | AMOUNT OF DPS* ADDED (LBS) | HEXA-CHLORO-DIOXINS | HEPTA-CHLORO-DIOXINS | OCTO-CHLORO-DIOXINS | TOTAL CHLORINATED DIOXINS |
|---|---|---|---|---|---|---|
| 34-2-1275 | mold | 0.125 | 89 | 458 | 2491 | 3039 |
| 46-2-275 | mold | 0.250 | 36 | 233 | 1215 | 1485 |
| 47-2-1275 | mold | 0.750 | 39 | 233 | 1542 | 1815 |
| 44-2-1275 | mold | 2.000 | 34 | 311 | 178 | 523 |
| 45-2-1275 | mold | 8.000 | 58 | 183 | 877 | 1118 |
| 16-2-1275 | mold | 0.000 (controls) | 258 | 938 | 2747 | 3944 |
| 18-2-1275 | mold | 0.000 (2nd control) | 200 | 763 | 3008 | 3972 |
| 19-2-1275 | mold | 0.000 (3rd control) | 196 | 890 | 3582 | 4668 |
| 29-2-1275 | shotted | 0.500 | 45 | 417 | 2180 | 2641 |
| 36-2-1275 | shotted | 0.750 | 47 | 329 | 2223 | 2629 |
| 10-2-1275 | shotted | 1.250 | 29 | 454 | 1868 | 2350 |
| 24-2-1275 | shotted | 4.000 | 18 | 210 | 1323 | 1551 |
| 26-2-1275 | shotted | 0.000 (control) | 154 | 670 | 2884 | 3709 |
| 13-2-1275 | shotted | 0.000 (2nd control) | 115 | 567 | 2428 | 3111 |

*Diphenyl sulfide

What is claimed is:

1. In a process for producing relatively pure commercially acceptable pentachlorophenol, comprising reacting at a temperature ranging from about 10° to about 190° C., (A) a phenol which is at least one member selected from a group consisting of phenol and lower chlorophenols and mixtures thereof, and (B) chlorine, in the presence of (C) an acid catalyst from about 0.005 moles to about 0.016 moles per mole of (A) used, consisting essentially of aluminum chloride, ferric chloride, metal iron, aluminum tris-butoxide, antimony chloride, metallic antimony, stannous chloride, metallic tin, cuprous chloride and metallic copper; the improvement consisting of using (D) a sulfur containing co-catalyst selected from the group consisting of sulfur thiophenol, para-chlorothiophenol, para, para'-dichlorophenyl sulfide, sodium hydrosulfide, 2,2'-thiobis (4,6-dichlorophenol) benzyl disulfide, dibenzothiophenol, benzyldisulfide, diphenyl sulfide, diphenyl disulfide, di-isopentyl sulfide, naphthalene thiol, heptyl sulfide, hexochlorophenyl sulfide, dicresyl disulfide, dihexadecyl sulfide and dibenzothiophenol thiophenol, wherein components (A) and (B) constitute the sole reacting ingredients and components (C) and (D) constitute the catalytic system for promoting the reaction of components (A) and (B).

2. The process as set forth in claim 1 wherein the co-catalyst is sulfur.

3. The process as set forth in claim 1 wherein the co-catalyst is thiophenol.

4. The process as set forth in claim 1 wherein the co-catalyst is diphenyl sulfide.

5. The process as set forth in claim 1 wherein the amount of co-catalyst used ranges from about 0.0001 moles to about 0.05 moles per mole of (A) used.

6. The process as set forth in claim 1 wherein the amount of co-catalyst used ranges from about 0.001 moles to about 0.05 moles per mole of (A) used.

7. In a process for producing relatively pure commercially acceptable pentachlorophenol, comprising reacting at a temperature ranging from about 10° to about 190° C., (A) phenol and (B) chlorine in the presence of (C) an acid catalyst from about 0.005 moles to about 0.016 moles per mole of (A) aluminum chloride, chloride, the improvement consisting of using (D) a co-catalyst selected from the group consisting of thiophenol and diphenyl sulfide, wherein components (A) and (B) constitute the sole reacting ingredients and components (C) and (D) constitute the catalytic system for promoting the reaction of components (A) and (B).

* * * * *